United States Patent [19]

Suzuki et al.

[11] Patent Number: 4,908,762
[45] Date of Patent: Mar. 13, 1990

[54] OXIMETER WITH SYSTEM FOR TESTING TRANSMISSION PATH

[75] Inventors: Susumu Suzuki; Sumio Yagi; Naotoshi Hakamata; Takeo Ozaki, all of Shizuoka, Japan

[73] Assignee: Hamamatsu Photonics Kabushiki Kaisha, Shizuoka, Japan

[21] Appl. No.: 188,910

[22] Filed: May 2, 1988

[30] Foreign Application Priority Data

May 8, 1987 [JP] Japan .................. 62-110471

[51] Int. Cl.$^4$ ............................ G06F 15/42
[52] U.S. Cl. .................. 364/413.09; 128/633; 356/41; 356/434
[58] Field of Search .............. 356/41, 434; 128/633, 128/664; 364/413.01, 413.09

[56] References Cited

U.S. PATENT DOCUMENTS

| | | | |
|---|---|---|---|
| 3,441,349 | 4/1969 | Daly et al. | 356/93 |
| 4,128,339 | 12/1978 | Yamazaki et al. | 356/434 |
| 4,223,680 | 9/1980 | Jobsis | 128/633 |
| 4,281,645 | 4/1983 | Jobsis | 128/633 |
| 4,321,930 | 3/1982 | Jobsis et al. | 128/633 |
| 4,380,240 | 4/1983 | Jobsis et al. | 128/633 |
| 4,510,938 | 4/1985 | Jobsis et al. | 128/633 |
| 4,603,700 | 8/1986 | Nichols et al. | 128/633 |

FOREIGN PATENT DOCUMENTS 2075668A 11/1981 United Kingdom .
2151020A 7/1985 United Kingdom .

OTHER PUBLICATIONS

Harper, B. M., "Optical transmission measurements using computer response correction", Review of Scientific Instruments, vol. 55, No. 4, pp. 499–502, Apr. 1984.
Tamura, M. et al., "Measurement of Living Body Near Infrared Light Spectrophotometry", Near–Infrared Tissue Spectroscopy, vol. 23, No. 4, pp. 377–385, 1986 (In Japanese).
Wyatt, J. S. et al., "Quantification of Cerebral Oxygenation and Haemodynamics in Sick Newborn Infants by Near Infrared Spectrophotometry", The Lancet, pp. 1063–1066, Nov. 8, 1986.

Primary Examiner—Jerry Smith
Assistant Examiner—David Huntley
Attorney, Agent, or Firm—Finnegan, Henderson, Farabow, Garrett and Dunner

[57] ABSTRACT

An examination apparatus measures the oxygenation in body organs by the near infrared light transmission spectrophotometry. To inspect the examination apparatus itself before the oxygenation measurement, an illumination-side fixture and a detection-side fixture have such structures that these fixtures can be assembled together in such a manner that near infrared light is directly made incident on the detection-side fixture from the illumination-side fixture. In the midst of the measurement, the examination apparatus is regularly inspected and a photomultiplier tube can be separately inspected by employing a separate light source for inspection.

9 Claims, 5 Drawing Sheets

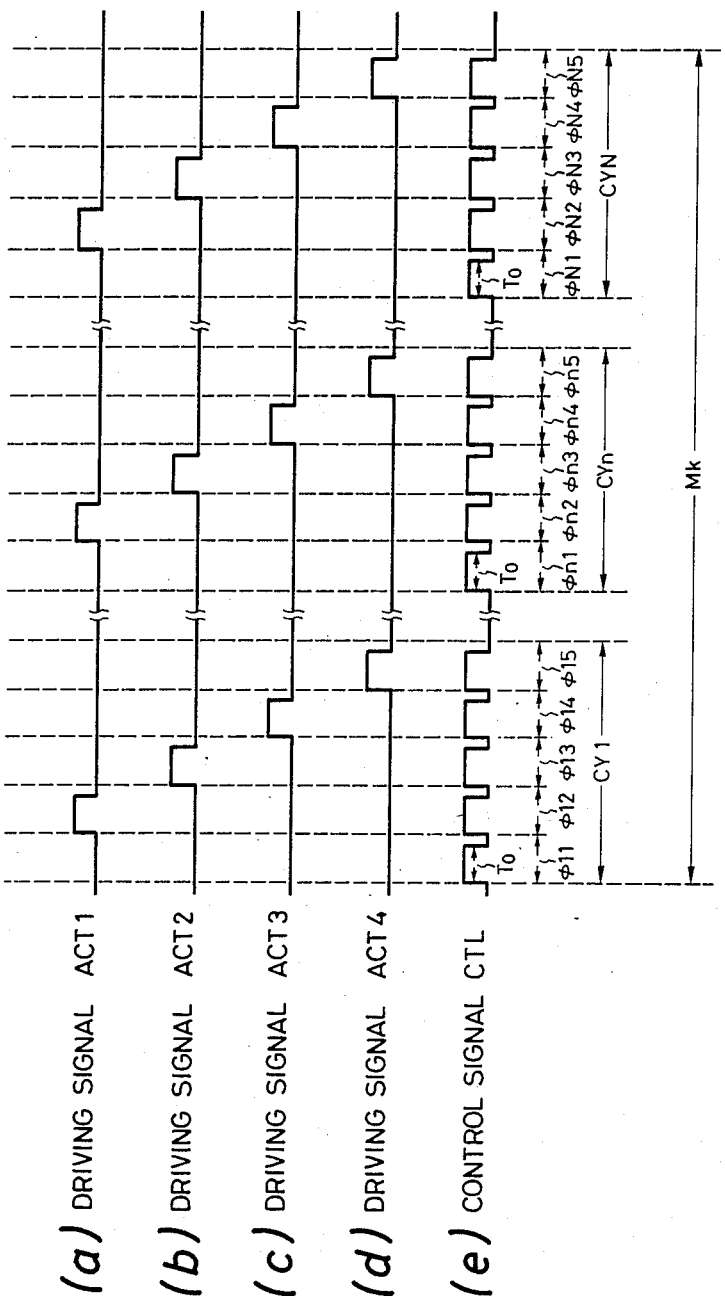

OXIMETER WITH SYSTEM FOR TESTING TRANSMISSION PATH

BACKGROUND OF THE INVENTION

The present invention relates to the apparatus for measuring the oxygen quantity in objects such as organs, e.g., the cerebral tissues of a human body or an animal. The invention especially relates to the apparatus for measuring the oxygenation of hemoglobin in blood and of cytochrome in cells by detecting those through electromagnetic waves.

In general, in diagnosing the function of a body organ, such as the cerebral tissues, the fundamental and important parameters to measure are the oxygen quantity in the body organ and the organ's utilization of oxygen. Supplying body organs with a sufficient quantity of oxygen is indispensable for the growth ability of fetuses and new-born infants. If the supply of oxygen to a fetus is insufficient, the probability that the fetus will not survive, or that the new-born infant will die are high. Even if the new-born infant lives, however, serious problems in the body organs may remain as sequelae. The insufficiency of oxygen affects every body organ, but especially causes serious damage in the cerebral tissues.

To examine the oxygen quantity in body organs readily and at the early stage of illness, an examination apparatus disclosed on Aug. 4, 1981 was developed. In this kind of examination apparatus, the variation of oxygen quantity in body organs, especially in the brain, is measured through the absorption spectrum of near infrared light. The absorption is caused by the hemoglobin which is an oxygen-carrying medium in blood and the cytochrome a, a$_3$ and which performs oxydation-reduction reaction in cells. As shown in FIG. 4(a), the absorption spectra of near infrared light (700 to 1300 nm), $\alpha_{HbO2}$ and $\alpha_{Hb}$ by oxygenated hemoglobin (HbO$_2$) and disoxygenated hemoglobin (Hb), respectively, are different from each other. As shown in FIG. 4(b), the absorption spectra of $\alpha_{CyO2}$ and $\alpha_{Cy}$ by oxidized cytochrome a, a$_3$ (CyO$_2$) and reduced cytochrome a, a$_3$ (Cy), respectively, are different from each other. This examination apparatus utilizes the above-described absorption spectra of near infrared light. Four near infrared light rays with different wavelengths, $\lambda_1$, $\lambda_2$, $\lambda_3$ and $\lambda_4$ (e.g. 775 nm, 800 nm, 825 nm and 850 nm) are applied to one side of the patient's head with a time-sharing method and the transmission light rays from the opposite side of the head are in turn detected. By processing these four detected light rays with the prescribed calculation program the density variations of oxygenated hemoglobin (HbO$_2$), disoxygenated hemoglobin (Hb), oxidized cytochrome a, a$_3$ (CyO$_2$) and reduced cytochrome a, a$_3$ (Cy) are calculated. These parameters, in turn, determine the variation of cerebral oxygen quantity.

FIG. 5 shows a system outline of the above-described conventional examination apparatus 45. The conventional examination apparatus 45 includes; light sources such as laser diodes LD1 to LD4 which emit four near infrared light rays with different wavelengths of $\lambda_1$, $\lambda_2$, $\lambda_3$ and $\lambda_4$, respectively; a light source control device 55 which controls output timing of the light sources LD1 to LD4; optical fibers 50-1 to 50-4 which introduces near infrared light rays emitted by the light sources LD1 to LD4 to a patient's head 40; an illumination-side fixture 51 which bundles and holds end portions of the optical fibers 50-1 to 50-4; a detection-side fixture 52 which is fitted to the prescribed position of the opposite side of the patient's head 40; an optical fiber 53 which is held by the detection-side fixture 52 and introduces transmitted near infrared light from the patient's head 40; a transmission light detection device 54 which measures transmission quantity of near infrared light by counting photons of near infrared light introduced by the optical fiber 53; and a computer system 56 which controls the total examination apparatus and determines the variation of oxygen quantity in cerebral tissues being based on the transmission quantity of near infrared light.

The computer system 56 is equipped with a processor 62, a memory 63, output devices 64 such as a display and a printer, and an input device 65 such as a keyboard, and these devices are connected to each other by a system bus 66. The light source control device 55 and the transmission light detection device 54 are connected to the system bus 66 as external I/O's.

The light source control device 55 receives instructions from the computer system 56 and drives the light sources LD1 to LD4 by respective driving signals ACT1 to ACT4 as shown in FIG. 6(a) to 6(d). As shown in FIG. 6 one measuring period M$_k$ (k=1, 2, . . .) consists of N cycles of CY1 to CYn. At a phase $\phi$n1 in an arbitrary cycle CYn, no light source of LD1 to LD4 is driven and therefore the patient's head 40 is not illuminated by the near infrared light from the light sources LD1 to LD4. At the phase $\phi$n2 light source LD1 is driven and the near infrared light with the wavelength of, for example, 775 nm is emitted from it. In the same manner, at the phase $\phi$n3 the light source LD2 is driven and the near infrared light with the wavelength of, for example, 800 nm is emitted from it; at the phase $\phi$n4 the light source LD3 is driven and the near infrared light with the wavelength of, for example, 825 nm is emitted from it; and at the phase $\phi$n5 the light source LD4 is driven and the near infrared light with the wavelength of, for example, 850 nm is emitted from it. In this manner the light source control device 55 drives the light sources LD1 to LD4 sequentially with a time-sharing method.

Referring again to FIG. 5, the transmission light detection device 54 is equipped with a filter 57 which adjusts the quantity of near infrared light outputted to lenses 70 and 71 from the optical fiber 53; a photomultiplier tube 58 which converts the light from the filter 57 into pulse current and outputs it; an amplifier 59 which amplifies the pulse current from the photomultiplier tube 58; an amplitude discriminator 60 which eliminates the pulse current from the amplifier 59 whose amplitude is smaller than the prescribed threshold value; a multichannel photon-counter 61 which detects photon frequency in every channel; a detection controller 67 which controls detection periods of the multi-channel photon-counter 61; and a temperature controller 68 which controls the temperature of a coller 69 containing the photomultiplier tube 58.

To use the above-described examination apparatus, the illumination-side fixture and the detection-side fixture are firmly fitted to the prescribed positions of the patient's head 40 by using tape or the like. Once fitted, the light sources LD1 to LD4 are driven by the light source control device 55 as shown in FIG. 6(a) to 6(d), respectively, so that the four near infrared light rays with different wavelengths are emitted from the light sources LD1 to LD4 sequentially with the time-sharing method, and the light rays are introduced by the optical fibers 50-1 to 50-4 to the patient's head 40. As bones and soft tissues in the patient's head 40 are transparent to the near infrared light, the near infrared light is partially absorbed by hemoglobin in blood and cytochrome a, $a_3$ in cells and outputted to the optical fiber 53. The optical fiber 53 introduces the light to the transmission light detection device 54. At the phase $\phi n1$ no light source of LD1 to LD4 is driven, and therefore, the transmission light detection device 54 detects dark light.

The photomultiplier tube 58 in the transmission light detection device 54 is used with a photon-counting device that has high sensitivity and operates at high response speed. The output pulse current from the photomultiplier tube 58 is sent to the amplitude discriminator 60 through the amplifier 59. The amplitude discriminator 60 eliminates the noise component whose amplitude is smaller than the prescribed amplitude threshold and sends only the signal pulse to the multi-channel photon-counter 61. The multi-channel photon-counter 61 detects photons only in the periods $T_o$. The periods to are synchronized with the driving signals ACT1 to ACT4 for the respective light sources LD1 to LD4 as shown in FIG. 6(a) to (d) by a control signal CTL as shown in FIG. 6(e). The control signal CTL is generated by the detection controller 67. The multi-channel photon-counter then counts detected photons of every light with each wavelength sent from the optical fiber 53. The transmission data of every near infrared light with each wavelength are obtained through the above-described procedure.

As shown in FIG. 6(a) to (e), at the phase $\phi n1$ in the cycle CYn of light source control device 55 no light source of LD1 to LD4 is driven, therefore the dark light data d are counted by the transmission light detection device 54. At the phases $\phi n2$ to $\phi n5$ the light sources LD1 to LD4 are sequentially driven with the time-sharing method and the transmission light detection device 54 sequentially counts the transmission data $t_{\lambda 1}$, $t_{\lambda 2}$, $t_{\lambda 3}$ and $t_{\lambda 4}$ of the respective near infrared light rays with different wavelengths $\lambda_1$, $\lambda_2$, $\lambda_3$ and $\lambda_4$.

The counting of the dark light data d and the transmission data $t_{\lambda 1}$, $t_{\lambda 2}$, $t_{\lambda 3}$ and $t_{\lambda 4}$ which is sequentially performed in the cycle CYn, is continued N times from CY1 to CYn. That is, one measuring period $M_k$ (k=1, 2, ...) includes N cycles. A concrete example is as follows; if one cycle is 200 μsec and N is 10000, the measuring period $M_k$ becomes 2 sec. At the time of finishing of one measuring period $M_k$, the counting result of the dark light data $$D\left(=\sum_{n=1}^{N} d/CYn\right)$$

and the counting results of the transmission data $$T_{\lambda 1}, T_{\lambda 2}, T_{\lambda 3} \text{ and } T_{\lambda 4}\left(=\sum_{n=1}^{N} t_{\lambda j}/CYn\right)$$

are transferred to the computer system 56 and stored in the memory 63.

The processor 62 performs the subtraction of the dark light component by using the combination of the transmission data and the dark data $(T_{\lambda 1}, T_{\lambda 2}, T_{\lambda 3}, T_{\lambda 4}, D)_{Mk}$ being stored in the memory 63 after one measuring period $M_k$ and the combination of those $(T_{\lambda 1}, T_{\lambda 2}, T_{\lambda 3}, T_{\lambda 4}, D)_{Mo}$ at the start of measuring, and calculates the variation rates of the transmission light $\Delta T_{\lambda 1}$, $\Delta T_{\lambda 2}$, $\Delta T_{\lambda 3}$ and $\Delta T_{\lambda 4}$. That is, the variation rates of the transmission light $\Delta T_{\lambda 1}$, $\Delta T_{\lambda 2}$, $\Delta T_{\lambda 3}$ and $\Delta T_{\lambda 4}$ are calculated as:

$$\Delta T_{\lambda j} = \log[(T_{\lambda j} - D)_{Mk}/(T_{\lambda j} - D)_{Mo}] (j=1 \text{ to } 4). \tag{1}$$

The use of logarithm in the above calculation of $\Delta T_{\lambda j}$ is to express the variation as an optical density.

Using the above-calculated variation rates of the transmission light $\Delta T_{\lambda 1}$, $\Delta T_{\lambda 2}$, $\Delta T_{\lambda 3}$ and $\Delta T_{\lambda 4}$, density variations of oxygenated hemoglobin ($HbO_2$), disoxygenated hemoglobin (Hb), oxidized cytochrome a, $a_3$ ($CyO_2$) and reduced cytochrome a, $a_3$ which are expressed as $\Delta X_{HbO_2}$, $\Delta X_{Hb}$, $\Delta X_{CyO_2}$ and $\Delta X_{Cy}$, respectively, can be determined. That is, each of density variations of $\Delta X_{HbO_2}$, $\Delta X_{Hb}$, $\Delta X_{CyO_2}$ and $\Delta X_{Cy}$ is calculated as:

$$\Delta X_i = \sum_{j=1}^{4} (\alpha_{ij})^{-1} \Delta T_{\lambda j}/l \tag{2}$$

where $\alpha_{ij}$ is an absorption coefficient of each component i ($HbO_2$, Hb, $CyO_2$, Cy) for each wavelength $\lambda_j$ ($\lambda_1$, $\lambda_2$, $\lambda_3$, $\lambda_4$) and is predetermined from FIG. 4(a) and (b), and l is the length of the patient's head 40 along the travelling direction of the near infrared light.

As the above-detected density variation components, $\Delta X_{HbO_2}$, $\Delta X_{Hb}$, $\Delta X_{CyO_2}$ and $\Delta X_{Cy}$, reflect the variation of oxygen in the brain, the variation of oxygen quantity in the brain can be determined by outputting these detected results from the output device 64. The diagnosis thus is made based on these results.

It is required in the foregoing examination apparatus that the transmission efficiency through the paths between the light sources LD1 to LD4 and the transmission light detection device 54 is always kept constant. Especially, the transmission efficiency through the paths between the light sources LD1 to LD4 and the photomultiplier tube 58 should be always kept constant.

But the above transmission efficiency is likely to be changed by following causes. Generally, as this kind of examination apparatus is frequently moved from one bed to another bed and the fixtures 51, 52 are frequently put on and off, the fixtures 51, 52 are likely to be damaged or stained, or the optical system such as the lenses 70, 71 is likely to get out of position. As the measurement of oxygenation sometimes lasts for twenty-four hours, the light sources LD1 to LD4 and the photomultiplier tube 58 are likely to be deteriorated.

Therefore, the examination apparatus in which the inspection of the light sources LD1 to LD4, fixtures 51, 52 and the optical system such as lenses 70, 71 and the photomultiplier tube 58 in the transmission light detection device 54 can be done before the measurement, is required. Especially, as the optical system such as the lenses 70, 71 and the photomultiplier tube 58 in the transmission light detection device 54 are delicate, the characteristics of those are likely to be changed. Therefore, the examination apparatus in which the inspection of those can be separately made, is also required.

Moreover, as the oxygenation measurement is continuously performed for a long time as described above, it happens during the measurement that the optical system gets out of position, the window of the photomultiplier tube 58 is clouded up by the cooling operation of the cooler 69, or the photomultiplier tube 58 is deteriorated. Accordingly, the examination apparatus in which the inspection of the optical system in the transmission light detection device and the photomultiplier tube 58 can be automatically done in the midst of the measurement, is required.

SUMMARY OF THE INVENTION

An object of the present invention is to provide an examination apparatus which can be easily and surely inspected.

An examination apparatus according to the present invention comprises a light source means which sequentially emit electromagnetic waves with different wavelengths, an illumination-side fixture which makes the electromagnetic waves from the light source means incident on a measuring object, and a detection-side fixture which receives transmitted electromagnetic waves from the measuring object and sends those to transmission light detection means.

In the first aspect of the invention, the illumination-side fixture and the detection-side fixture can be assembled together so that the electromagnetic wave is directly made incident on the detection-side fixture from the illumination-side fixture. By employing these fixtures an inspection of the examination apparatus can be done before the oxygenation measurement. That is, these fixtures are assembled together, the electromagnetic wave emitted from the light source means is made incident on the transmission light detection means through these fixtures, and a transmission light quantity is detected by the transmission light detection means. A whole transmission path of the examination apparatus can be inspected by examining if the detected transmission light quantity is optimum.

In the second aspect of the invention, an inspection light source is additionally equipped in the examination apparatus, which is driven in a period when the above light source means is not driven so that an inspection electromagnetic wave emitted from the inspection light source is made incident on the transmission light detection means. By employing this structure, especially the inspection of only the transmission light detection means can be done before and in the midst of the oxygenation measurement. That is, the inspection light source is driven in a period when the light source means is not driven so that an inspection electromagnetic wave is emitted from the inspection light source, the inspection electromagnetic wave is sent to the transmission light detection means, and a transmission light quantity only through a path in the transmission light detection means is detected. A transmission path within the transmission light detection means can be inspected by examining if the transmission light quantity thus detected is optimum.

In the third aspect of the invention, the examination apparatus comprises the above-described inspection light source and output light detection means which detects output light quantities from the light source means and the inspection light source. Furthermore, the examination apparatus comprises the illumination-side fixture and the detection-side fixture with the structure of the above-described first aspect. Before the oxygenation measurement the whole transmission path of the examination apparatus can be inspected in the same manner as in the first aspect. Moreover, by sending the electromagnetic wave from the light source means to the output light detection means and thereby detecting an output light quantity, it can be inspected if the light source means is deteriorated. In precisely inspecting the transmission light detection means, the inspection light source is driven instead of the light source means, so that the transmission path within the transmission light detection means can be inspected in the same manner as in the second aspect. During the measurement, the transmission path within the transmission light detection means can be inspected by driving the inspection light source in the same manner as in the second aspect. Furthermore, the transmission path within the transmission light detection means can be inspected more precisely by detecting an inspection light quantity emitted from the inspection light source by the output light detection means and normalizing the obtained transmission light quantity through the path in the transmission light detection means by the inspection light quantity.

Other and further objects, features and advantages of the invention will appear more fully from the following description taken in connection with the attached drawings.

BRIEF DESCRIPTION OF THE DRAWINGS

FIG. 6(a) to (e) are time-charts of driving signals ACT1 to ACT4 and a control signal CTL, respectively.

DETAILED DESCRIPTION OF THE PREFERRED EMBODIMENTS

Embodiments of the present invention will be described in the following being based on the attached drawings.

Figure 1:
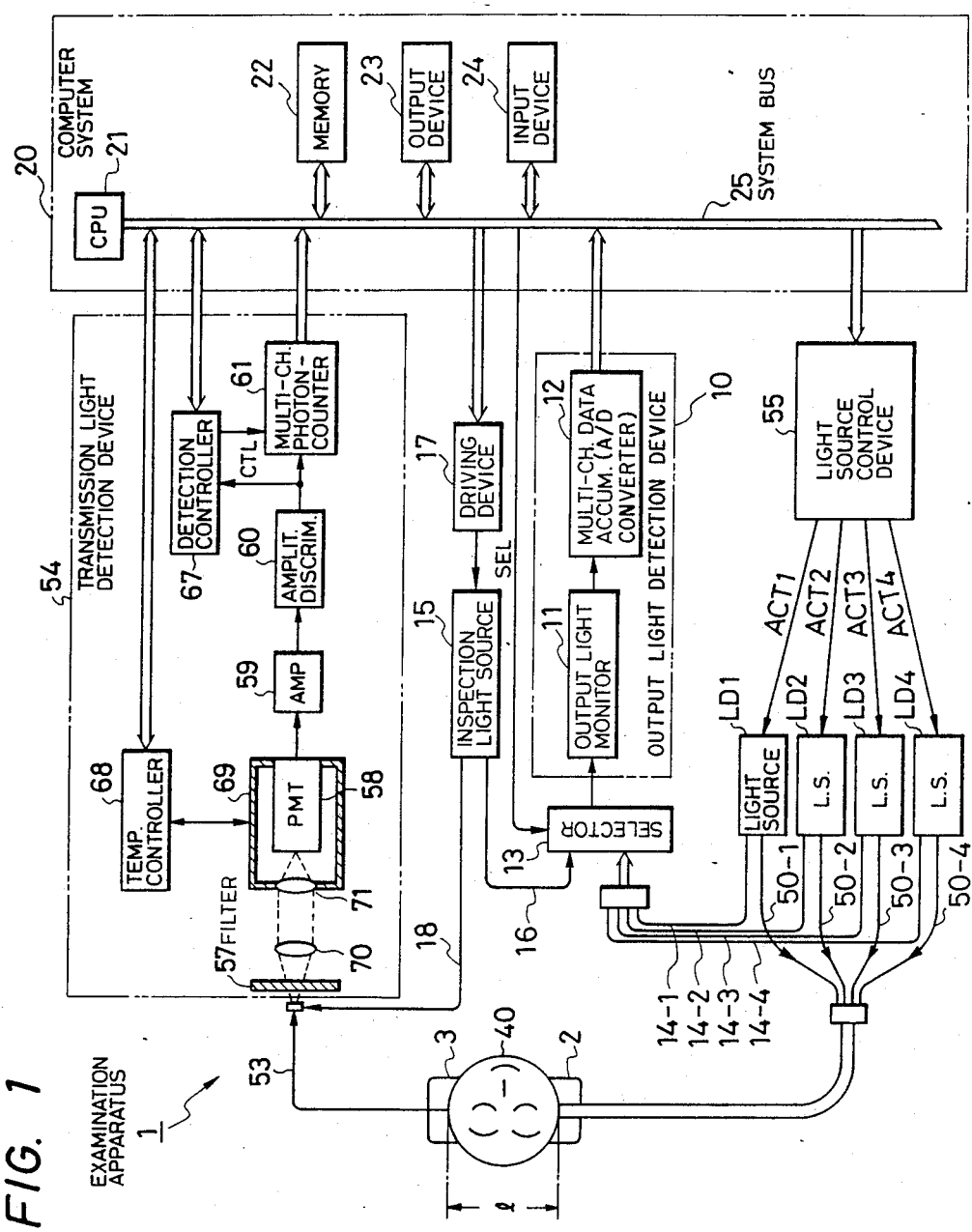
FIG. 1 is a block diagram showing a system constitution of an examination apparatus according to an embodiment of the present invention.
Figure 2:
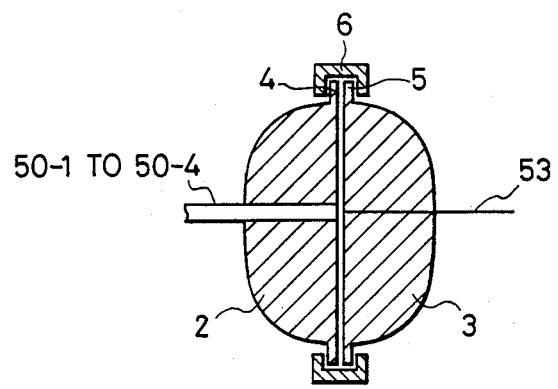
FIG. 2 is a sectional view showing an assembly of an illumination-side fixture and a detection-side fixture according to an embodiment of the invention.
Figure 5:
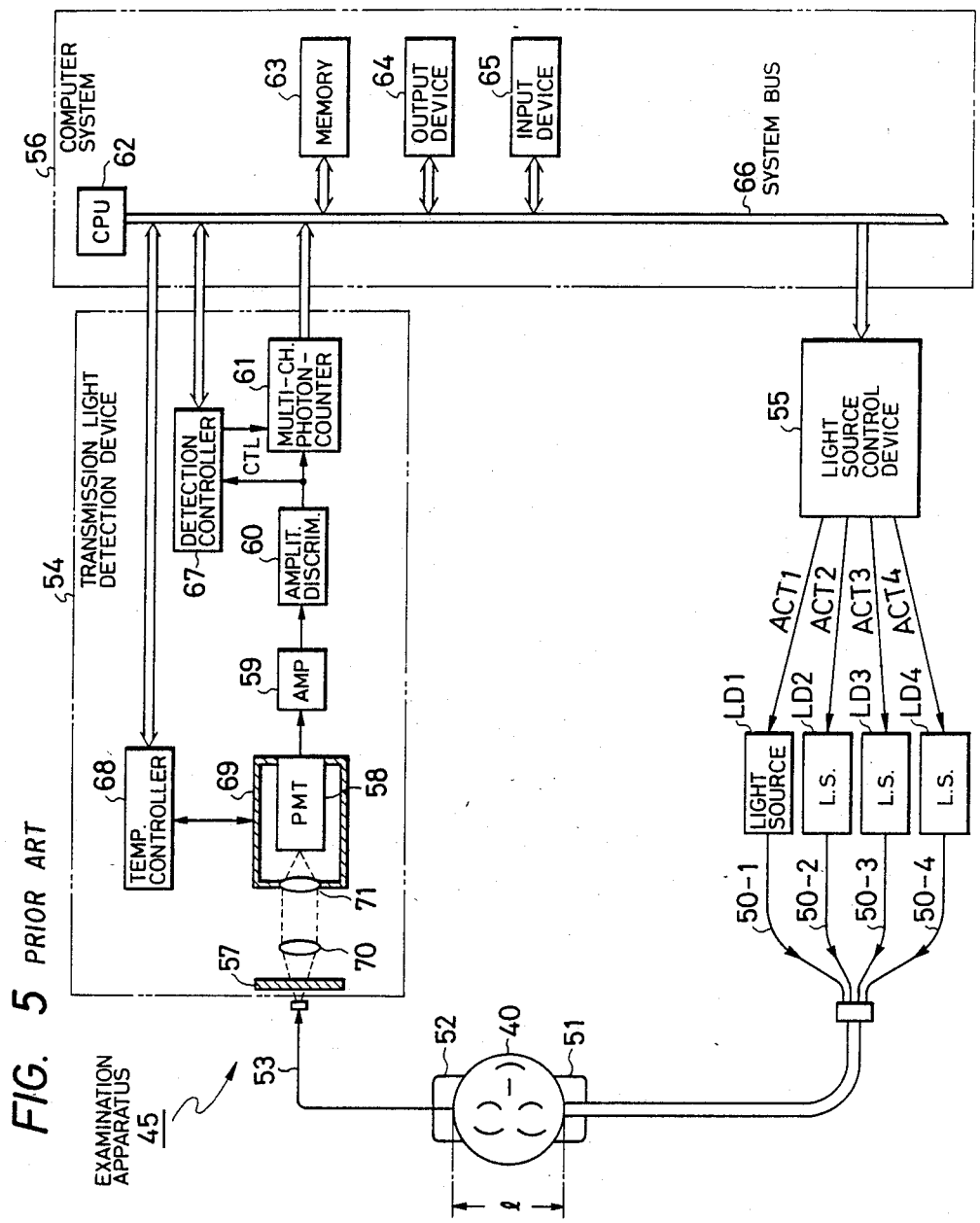
FIG. 5 is a block diagram showing a system constitution of a conventional examination apparatus.

FIG. 1 is a block diagram showing an examination apparatus according to an embodiment of the invention. In FIG. 1, blocks, parts and signals which are common to those in FIG. 5 are designated by the same reference numerals or characters as those in FIG. 5. In the examination apparatus 1, optical fibers 50-1 to 50-4 are held by an illumination-side fixture 2 and an optical fiber 53 is held by a detection-side fixture 3 in the same manner as in the conventional examination apparatus 45. The illumination-side fixture 2 and the detection-side fixture 3 have respective flanges in peripheries of their surfaces coming into contact with each other. The illumination-side fixture 2 and detection-side fixture 3 are fitted to for example a head 40 of an object person as shown in FIG. 1 in the oxygenation measurement. On the other hand, when the examination apparatus 1 is stored or had the custody of, or is inspected before the measurement, the fixtures 2 and 3 are made opposed and in close contact with each other by fitting a clasper 6 into the flanges 4 and 5 as shown in FIG. 2.

Figure 3:
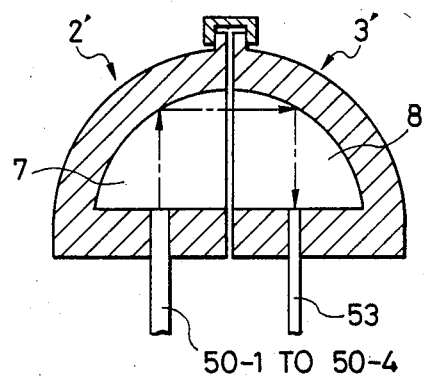
FIG. 3 is a sectional view showing another assembly of an illumination-side fixture and a detection-side fixture according to an embodiment of the invention.
Figure 4A:
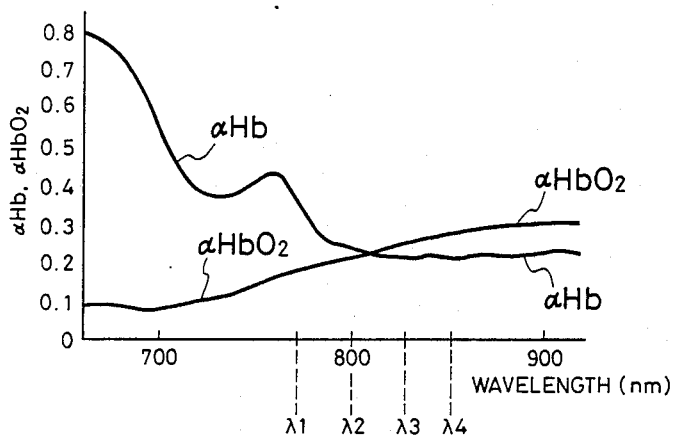
FIG. 4(a) and (b) are graphs showing absorption spectra of hemoglobin and cytochrome, respectively.
Figure 4B:
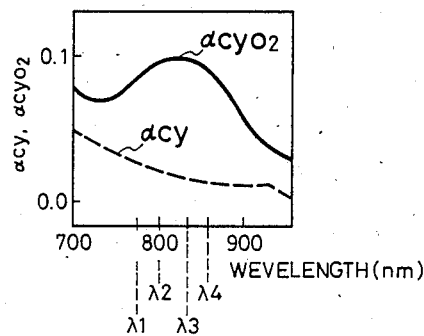

FIG. 3 shows another embodiment of the fixtures. The illumination-side fixture 2' and the detection-side fixture 3' in FIG. 3 are equipped with respective optical members such as prisms 7 and 8 inside those, so that a light path is changed by a prescribed angle, for example 90 degrees. By connecting the optical fibers 50-1 to 50-4 and 53 to respective prescribed surfaces of the prisms 7 and 8, the optical fibers 50-1 to 50-4 and 53 are kept in a natural state without being forced to bend when the fixtures 2' and 3' are fitted to each other. Instead of fitting the fixtures to each other by an external member such as the clasper 6 as in FIGS. 2 and 3, means for fitting the fixtures may be included in the fixtures themselves.

The examination apparatus 1 shown in FIG. 1 is equipped with an output light detection device 10. The output light detection device 10 comprises an output light monitor 11 consisting of for example a photodiode, and a multi-channel data accumulator 12 which A/D-converts an analog electric signal from the output light monitor 11, accumulates A/D-converted output light quantity and outputs accumulated date as output light quantity data.

A selector 13 is connected to the output light detection device 10. Optical fibers 14-1 to 14-4 which introduce respective near infrared light rays emitted from the light sources LD1 to LD4, and an optical fiber 16 which introduces inspection light emitted from an inspection light source 15, are connected to the selector 13. The selector 13 selects light which should be sent to the output light detection device 10 out of the near infrared light rays from the optical fibers 14-1 to 14-4 and the inspection light from the optical fiber 16 according to a selection signal SEL sent from a computer system 20.

The inspection light source 15 is used to inspect the light transmission path within the transmission light detection device 54 before or during the measurement and is driven by an inspection light source driving device 17 under the control of the computer system 20. Output light rays emitted from the inspection light source 15 are sent to the selector 13 through the optical fiber 16, and to the transmission light detection device 54 through the optical fiber 18 so as to inspect if the optical system such as lenses 70 and 71 is kept in its normal position, if the window of the photomultiplier tube 58 is kept clear, and if the photomultiplier tube 58 has not been deteriorated.

In the computer system 20, a processor 21, a memory 22, an output device 23 and an input device 24 are connected to a system bus 25 in the same manner as in the conventional computer system 56. Furthermore, the computer system 20 has a function to inspect the examination apparatus 1 before and during the measurement.

The operation of the examination apparatus 1 with the foregoing constitution will be described in the following. First, to inspect the examination apparatus 1 before the oxygenation measurement, the illumination-side fixture 2 and the detection-side fixture 3 are made in close contact with each other as shown in FIG. 2. The computer system 20 gives instruction to the light source control device 55 so that near infrared light rays with different wavelengths $\lambda 1$ to $\lambda 4$ are sequentially emitted from the respective light sources LD1 to LD4. The near infrared light rays from the light sources LD1 to LD4 are introduced by the respective optical fibers 50-1 to 50-4 to the illumination-side fixture 2, directly made incident on the detection-side fixture 3 from the illumination-side fixture 2, and sent to the transmission light detection device 54 through the optical fiber 53. In the transmission light detection device 54, the near infrared light rays with different wavelengths $\lambda 1$ to $\lambda 4$ are sent to the photomultiplier tube 58 through a filter 57 and the lenses 70 and 71, path-transmission light quantities are counted by a multi-channel photon-counter 61 at every wavelength, and counted results (prescribed times, for example N times of counting) are sent to the computer system 20. The counted results are stored in the memory 22 of the computer system 20 as path-transmission light data $TR_{\lambda 1}$, $TR_{\lambda 2}$, $TR_{\lambda 3}$ and $TR_{\lambda 4}$.

The near infrared light rays emitted from the light sources LD1 to LD4 are also sent to the selector 13 through the respective optical fibers 14-1 to 14-4 as well as sent to the optical fibers 50-1 to 50-4. The selector 13 selects the near infrared light rays introduced from the optical fibers 14-1 to 14-4 according to the selection signal SEL sent from the computer system 20 and sends the selected near infrared light rays to the output light detection device 10. The output light detection device 10 accumulates at every wavelength output quantities of the near infrared light rays with different wavelengths $\lambda 1$ to $\lambda 4$ sequentially sent from the respective light sources LD1 to LD4 and sends accumulation results to the computer system 20 after the accumulation of prescribed times, for example N times. The accumulation results are stored in the memory 22 of the computer system 20 as the output light data $I_{\lambda 1}$, $I_{\lambda 2}$, $I_{\lambda 3}$ and $I_{\lambda 4}$. In the memory 22 of the computer system 20 there stored in advance are output light data $I_{\lambda 10}$, $I_{\lambda 20}$, $I_{\lambda 30}$ and $I_{\lambda 40}$ which correspond to respective optimum light output powers of the light sources LD1 to LD4, and path-transmission light data $TR_{\lambda 10}$, $TR_{\lambda 20}$, $TR_{\lambda 30}$ and $TR_{\lambda 40}$ which should be obtained when the photomultiplier tube 58 is in an optimum condition.

The processor 21 compares the path-transmission light data $TR_{\lambda 1}$ to $TR_{\lambda 4}$ and the output light data $I_{\lambda 1}$ to $I_{\lambda 4}$ stored in the memory 22 with the respective optimum path-transmission light data $TR_{\lambda 10}$ to $TR_{\lambda 40}$ and the respective optimum output light data $I_{\lambda 10}$ to $I_{\lambda 40}$ also stored in the memory 22 so as to check if the path-transmission light data and the output light data are optimum. The results of the comparison are outputted to the output device 23, such as a printer or a display.

If one of the output light data $I_{\lambda 1}$ to $I_{\lambda 4}$ is much different from the corresponding one of the optimum output light data $I_{\lambda 10}$ to $I_{\lambda 40}$, the indication may be that the corresponding one of the light sources LD1 to LD4 has deteriorated or is not adjusted to the optimum condition.

If one of the path-transmission light data $TR_{\lambda 1}$ to $TR_{\lambda 4}$ is much different from the corresponding one of the optimum path-transmission light data $TR_{\lambda 10}$ to $TR_{\lambda 40}$ while the output light data $I_{\lambda 1}$ to $I_{\lambda 4}$ have normal values, the indication may be that the illumination-side fixture 2 or detection-side fixture 3 has been damaged or stained, the optical system such as the lenses 70, 71 are out of position, or the photomultiplier tube 58 has deteriorated or the window of the photomultiplier to be 58 has clouded up. When only the optical system such as the lenses 70 and 71 and the photomultiplier tube 58, which are most delicate and whose characteristics are likely to change, are inspected, the inspection light emitted from the inspection light source 15 is directly introduced to the transmission light detection device 54. In this case the selector 13 selects the light from the inspection light source 15 according to the selection signal SEL. In this manner, the optical system and the photomultiplier tube 58 can be inspected more surely by directly sending the inspection light emitted from the inspection light source 15 to the transmission light detection device 54 and obtaining the path-transmission light data TS.

Besides the inspection performed before the measurement begins, as described above, the inspection can be performed also in the midst of the measurement of the oxygenation. In the measurement the illumination-side fixture 2 and the detection-side fixture 3 are fitted to for example the head 40 as shown in FIG. 1. As described in the foregoing, the light sources LD1 to LD4 are sequentially driven so as to emit the near infrared light rays and the near infrared light rays are made incident on the head 40 through the respective optical fibers 50-1 to 50-4 and the illumination-side fixture 2. Then, the near infrared light rays transmitted from the head 40 are sent to the transmission light detection device 54 through the detection-side fixture 3 and the optical fiber 53, the transmission quantities are counted in the transmission light detection device 54, and the results counted over one measuring period $M_k$ are sent to the computer system 20. The oxygenation measurement is performed with one measuring period $M_k$ ($k=1, 2, \ldots$) as a measuring unit. In the examination apparatus shown in FIG. 1, inspection period is inserted after repeating the measuring period $M_k$ prescribed times, for example m times ($k=1$ to m). In the inspection period, the computer system 20 sends the selection signal SEL to the selector 13 so that the selector 13 provides the output light detection device 10 with the light emitted from the inspection light source 15. The computer system also controls the inspection light source driving device 17 so as to drive the inspection light source 15. The inspection light emitted from the inspection light source 15 is introduced to the transmission light detection device 54 by the optical fiber 18 and sent to the photomultiplier tube 58 through the optical system such as the filter 57 and the lenses 70 and 71. The path-transmission light data TS are obtained in the multi-channel photon-counter 61 and stored in the memory 22 of the computer system 20 at the end of the inspection period.

On the other hand, the light emitted from the inspection light source 15 is also introduced to the output light detection device 10 by the optical fiber 16. The output light data IS are obtained through the accumulation in the output light detection device 10 and stored in the memory 22 of the computer system 20 at the end of the inspection period.

The processor 21 confirms that the output power of the inspection light source 15 is appropriate being based on the output light data IS. Then, the processor 21 judges if the path-transmission light data TS are proper. The result of judgement is outputted from the output device 23. If the above-detected path-transmission light data TS are different from the previously determined optimum path-transmission data $TS_{10}$ to $TS_{40}$, the indication is that the optical system such as the lenses 70 and 71 or the photomultiplier tube 58 is not in the normal condition.

As the inspection period is inserted after the prescribed times (e.g. m times) of the measurement, the examination apparatus 1 can be regularly inspected in the midst of the long-time measurement without stopping the operation.

As described in the foregoing embodiments, before the oxygenation measurement the examination apparatus 1 is automatically inspected with the illumination-side fixture 2 and detection-side fixture 3 assembled together in the same manner as when they are stored, and the inspection result is outputted from the output device 23. Therefore, the inspection of the examination apparatus 1 can be done quickly and accurately without a complicated operation. In the midst of the measurement, the inspection is regularly performed by inserting the inspection period after the prescribed times of the oxygenation measurement and the inspection results are outputted from the output device 23. Therefore, the inspection can be done quickly and accurately without stopping the measurement and the operator can know the condition of the examination apparatus 1 being based on the inspection results outputted from the output device 23.

Though the plural light sources are employed in the foregoing embodiments, the electromagnetic waves with different wavelengths may be obtained by using one white light source and filtering the white light emitted from the white light source. Moreover, the application of the examination apparatus of the invention is not limited to a medical field, but covers many fields including more measurements. The measuring object is not limited to body organs but may be general objects such as a piece of flesh. Furthermore, the electromagnetic wave emitted from the light source is not limited to near infrared light but may be far infrared light, visible light or microwave, etc.

What is claimed is:

1. An examination apparatus for measuring the oxygenation in an object with electromagnetic wave transmission spectrophotometry, comprising:
   a light source means for sequentially emitting electromagnetic waves housing different wavelengths;
   an illumination-side fixture for receiving said electromagnetic waves emitted from said light source means and outputting said electromagnetic waves;
   a detection-side fixture for detecting electromagnetic waves output from said illumination-side fixture and for sending said transmitted electromagnetic waves to a transmission light detection means;
   said transmission light detection means for detecting electromagnetic waves sent from said detection-side fixture and for outputting path-transmission light data; and
   a computer system for receiving said path-transmission light data from said transmission light detection means and for judging whether said examination apparatus is in an optimum condition on the basis of said path-transmission light data: wherein said illumination-side fixture and said detection-side fixture have such structures that said fixtures can be assembled together so that electromagnetic waves output from said illumination-side fixture are directly made incident on and detected by said detection-side fixture and said computer system includes a memory means for storing previously obtained optimum path-transmission light data and includes a processor means for comparing said path-transmission light data to said previously obtained optimum path-transmission light data.

2. An examination apparatus as claimed in claim 1, wherein said electromagnetic waves are near infrared light rays.

3. An examination apparatus for measuring the oxygenation in an object with electromagnetic wave transmission spectrophotometry, comprising:
   a light source means for sequentially emitting electromagnetic waves with different wavelengths;

an illumination-side fixture for receiving said electromagnetic waves emitted from said light source means and outputting said electromagnetic waves;

a detection-side fixture for detecting electromagnetic waves output from said illumination-side fixture and for sending said transmitted electromagnetic waves to a transmission light detection means;

an inspection light source means for outputting an inspection electromagnetic wave according to an instruction from a computer system and sending said inspection electromagnetic wave to the transmission light detection means;

said transmission light detection means for detecting electromagnetic waves output from said illumination-side fixture and for detecting said inspection electromagnetic wave and outputting first path-transmission light data; and said computer system for receiving said first path-transmission light data from said transmission light detection means and judging whether said transmission light detection means is in an optimum condition: wherein said computer system has a memory means for storing previously obtained optimum first path-transmission light data and a processor means for comparing said first path-transmission light data to said previously obtained optimum first path-transmission light data.

4. An examination apparatus as claimed in claim 3, wherein said electromagnetic waves and said inspection electromagnetic wave are near infrared light rays.

5. An examination apparatus as claimed in claim 3, wherein said inspection electromagnetic wave is emitted from said inspection light source means in a period when said electromagnetic waves are not emitted from said light source means in the midst of the oxygenation measurement.

6. An examination apparatus as claimed in claim 3, further comprising:

an output light detection means for detecting said electromagnetic waves emitted from said light source means or said inspection electromagnetic wave emitted from said inspection light source means and outputting output light data of said light source means or outputting output light data of said inspection light source means; wherein said computer system further receives said output light data of said light source means or said output light data of said inspection light source means and further judges whether light source means or inspection light source means is in an optimum condition; and said computer system has a memory means for storing previously obtained optimum light data and a processor means for comparing said output light data of said light source means or said output light data of said inspection light source means to said previously obtained optimum output light data.

7. An examination apparatus as claimed in claim 6, wherein said electromagnetic waves and said inspection electromagnetic wave are near infrared light rays.

8. An examination apparatus as claimed in claim 6, further comprising:

a selector for receiving said electromagnetic waves emitted from said light source means and said inspection electromagnetic wave emitted from said inspection light source means, selecting either said electromagnetic waves emitted from said light source means or said inspection electromagnetic wave emitted from said inspection light source means to be sent to said output light detection means according to an instruction from said computer system.

9. An examination apparatus as claimed in claim 3, wherein said illumination-side fixture and said detection-side fixture have such structures that said fixtures can be assembled together so that electromagnetic waves outputted from said illumination-side fixture are directly made incident on and detected by said detection-side fixture;

said transmission light detection means further outputs second path-transmission light data in response to said electromagnetic waves sent from said detection-side fixture;

said computer system further receives said second path-transmission light data from said transmission light detection means and judges whether said examination apparatus is in an optimum condition; and said memory means further stores previously obtained optimum second path-transmission light data and said processor means further compares said second path-transmission light data to said previously obtained optimum second path-transmission light data.

* * * * *